United States Patent [19]

Jones

[11] Patent Number: 4,950,989

[45] Date of Patent: Aug. 21, 1990

[54] MAGNETIZING HEAD CONSTRUCTION AND RELATED METHOD

[76] Inventor: Larry E. Jones, 2084 McCrays Mill Rd., Sumter, S.C. 29154

[21] Appl. No.: 285,057

[22] Filed: Dec. 15, 1988

[51] Int. Cl.$^5$ .................. G01N 27/84; G01R 33/12
[52] U.S. Cl. .................. 324/216; 335/284; 324/228
[58] Field of Search .................. 324/214–216, 324/207, 208, 228, 260; 335/284; 361/143, 152; 310/12, 13, 14; 336/221, 223, 233, 234

[56] References Cited

U.S. PATENT DOCUMENTS

| | | | |
|---|---|---|---|
| 3,335,377 | 8/1967 | Kohlhagen | 335/284 |
| 3,344,345 | 9/1967 | Moline | 324/215 |
| 3,624,572 | 11/1971 | Mallinson et al. | 335/284 X |
| 3,763,423 | 10/1973 | Forster | 324/224 |
| 4,611,169 | 9/1986 | Hermann | 324/208 |
| 4,694,247 | 9/1987 | Meili et al. | 324/216 |

OTHER PUBLICATIONS

Metals Handbook, 8th Edition, vol. 11, American Society for Metals, 1976, pp. 44–54.

Primary Examiner—Reinhard J. Eisenzopf
Assistant Examiner—Warren S. Edmonds
Attorney, Agent, or Firm—Dority & Manning

[57] ABSTRACT

A flux scanner head generates a unidirectional magnetic field external to the head adjacent a scanning surface thereof. Workpieces to be subjected to magnetic particle inspection may be successively passed through, held in, or otherwise associated with, the unidirectional field at different angles to achieve magnetization along multiple axes, without physical or electrical contact with the workpiece. The scanner head is usable with both residual and continuous methods of magnetic particle inspection, and as either a hand-held or fixed-mount system. The scanner head itself incorporates a coil having a plurality of turns with a ferromagnetic core separating such turns so as to intensify and direct outward and external to the surface of the scanner head the magnetic field generated by current flow through the coil.

34 Claims, 5 Drawing Sheets

MAGNETIZING HEAD CONSTRUCTION AND RELATED METHOD

BACKGROUND OF THE INVENTION

The present invention concerns improved nondestructive testing of a workpiece, in general, and in particular an improved scanner head and corresponding method for magnetic particle inspection of a magnetizable workpiece.

One widely known nondestructive test for discontinuities or cracks in ferromagnetic materials is magnetic particle inspection. It is known that magnetizing a ferromagnetic workpiece will cause opposing magnetic fields, that is flux leakages, to form at discontinuities in the workpieces. Application of magnetic particles, in either a wet or dry medium, to a magnetized ferromagnetic material will cause attraction of such magnetic particles in the areas of such flux leakages.

With experience, testing technicians can discern the differences between attraction of magnetic particles to cracks or the like in the workpiece versus the attraction pattern of magnetic particles to sharp edges or other intended features of the workpiece. Various methodologies relating to the general concepts of magnetic particle testing or inspection are well known to those of ordinary skill in the art of nondestructive inspection, as exemplified by the section entitled "Magnetic-Particle Inspection" at pages 44 through 74 of the *Metals Handbook*, 8th edition, Volume 11, "Nondestructive Inspection and Quality Control", by the American Society for Metals, 1976. Certain magnetic particle inspection techniques are also known by the term "magnafluxing".

Generally, in order to adequately test a workpiece, successive magnetization steps must be undertaken so that the article to be inspected is magnetized in at least two directions, normally approximately 45° to 90° from each other. Often, the two required directions of magnetization are obtained, as a practical matter by different methods of producing a magnetic field. As one example, a round shaft can be magnetized in a circular direction by physical contact with the shaft resulting in the passing of a current therethrough. Using well known magnetic field theory, such operation provides only one direction of magnetization of the round shaft. Another direction of magnetization may be obtained by placing the shaft within a coil, which would result in a longitudinally directed magnetization.

Even from the foregoing very simple-shaped workpiece example, it may be seen that considerable skilled handling and manipulation of the workpiece is required in order to effect multi-axis magnetization. As the complexity of the workpiece increases, so does the complexity and challenge of performing magnetic particle inspection on the workpiece.

In addition to the foregoing technical problems associated with physically manipulating and handling a workpiece, often requiring a highly experienced technician for successful testing operations, certain conventional testing procedures can result in damage to the workpiece. For example, whenever current is physically passed through a workpiece, electrical and physical contact with such workpiece is needed. Thus, in view of the sometimes thousands of ampere currents involved, a danger of arcing and burning the part exists. Moreover, workpiece areas adjacent to or near contact points (such as underneath a contact pad) cannot be inspected, requiring additional steps to obtain 100% coverage of the workpiece being inspected.

It is also a general aspect of conventional magnetic particle inspection procedures that current requirements for adequate magnetization increase considerably in direct relation to increasing size of the workpiece to be tested. Of course, significant increases in current levels correspondingly increases the potential for arcing and burning.

Still further, concern and experience must typically be brought to bear in determining the best (i.e., most efficient and safest) testing methodology to effect the magnetic particle inspection for a given workpiece. Whenever a coil is used for magnetization, the workpiece itself must be able to fit inside the coil. In addition, close attention must be paid to the relative closeness of the workpiece outside diameter to the coil inside diameter (i.e., the fill factor of the coil). Calculations for the required current are conventionally based on the length to diameter ratio of the workpiece, during such coil magnetizations. On occasion, pole pieces are needed to adjust this ratio into accepted or available amperage ranges. Accordingly, manipulation of the workpiece and rearrangement of the testing layout between successive magnetization steps, particularly for larger and/or odd-shaped pieces, is a very time consuming process.

In addition to magnetization with coils, magnetic yokes are known for providing magnetization in two directions by successively placing the yoke in different positions over the area of the workpiece to be tested. Normally, such yokes require physical contact with the part, which leads to obvious difficulties and disadvantages in connection with the testing of complex shaped parts. Accordingly, thorough testing of a given workpiece for either large or complex shaped parts is also time consuming whenever magnetic yokes are utilized.

Another magnetization methodology which can provide twin directional magnetization with subsequent operations involves use of a prod. Like yokes, prods can be applied in different positions to the workpiece of interest, resulting in magnetic field direction manipulation. Prods all normally involve electrical and physical contact with the part. Since use of a prod in essence results in small area contact with the workpiece, there is a considerably increased danger of burning the workpiece surface due to arcing.

Still further magnetic particle inspection methodologies are known, but commonly share operational difficulties or drawbacks when adapting same to variety in sizes and shapes of a workpiece. Also, larger parts to be tested commonly preclude use of small portable power supply-driven testing units due to their relatively larger power consumption requirements.

In all of the foregoing instances where physical set-ups and interconnections with the workpiece being tested must be determined and altered during successive steps, testing is relatively slow and tedious. Obviously, the more difficult it is to test a given piece, the more likely the possibility of improper or inadequate (e.g., incomplete) testing of such given workpiece. It may often be the case that complex shaped pieces which are relatively more difficult to test may in fact have a relatively greater need for testing due to additional processing steps in which they may have been involved in order to achieve their complex shape, since it is well known that processing steps such as cutting, grinding, or the like can introduce discontinuities, cracks, or other imperfections which are sought to be detected by use of magnetic particle inspections.

U.S. Pat. Nos. 4,694,247, issued to Meili et al., and 3,763,423, issued to Forster, are cited as examples of magnetic particle testing technology. The general teachings of such references as relates to known magnetic particle testing theories and the like are incorporated herein by reference, for additional general background of nondestructive magnetic particle testing.

More particularly, Meili et al. discloses a magnetic yoke type magnetization device which to some extent avoids direct physical contact with the workpiece. Elongated cylindrical or polygonal-shaped parts, i.e. long shafts, may be tested by rotating same about their axis, while also advancing same longitudinally along a cushion of dry magnetic material applied to the surface of the workpiece in the area of an adjacent magnetic yoke leg. While there is a degree of non-contact as between the magnetization device and the workpiece, the types of workpieces which may be treated with the Meili et al. device are very strictly limited. In others words, the Meili et al. teachings are not useful for general magnetization purposes, particularly for shapes other than long shafts. Also, the Meili et al. structure is rather involved, which does not suggest practical portability thereof.

Forster similarly relates to magnetization of an elongated workpiece being conveyed along a path by first and second test stations. The test stations incorporate a pair of orthogonally related magnetizing cores and respective energizing windings. The platelike core members each have a respective energizable winding, with an edge of each plate-like core being disposed closely adjacent passing surfaces of the workpiece. Thus, magnetization is effected with a narrower side edge of a plate-like core, rendering the Forster structure efficient primarily only with the elongated billet-type workpieces illustrated, such as having rectangular, circular, or hexagonal crosssections.

SUMMARY OF THE INVENTION

The present invention recognizes and addresses the foregoing matters and others regarding magnetic particle inspection methodologies. Hence, it is one general object of the present invention to provide for improved magnetic particle inspection. It is another general object to provide both a device for generating magnetic field particularly adapted for magnetic particle inspection uses, as well as an improved method of using such a device.

Another general object of this invention is to provide a device and method for magnetization that is capable of magnetizing workpieces in two or more directions without having electrical or physical contact with the workpiece. As a result, it is a more particular object to be able to process without difficulty workpieces of even great variety in size and shape, as well as to be able to process relatively larger parts using a relatively smaller power supply. In addition to the foregoing, it is a more specific object to be able to process all such workpieces faster than prior devices or methods requiring electrical or physical contact with workpieces.

Yet another more particular object is to avoid the disadvantages such as burning or arcing which can occur whenever an electrical or physical contact between a magnetizing instrument and the workpiece to be inspected is required.

Yet another general object is to provide a device for performing operations as a magnetizing or flux scanner head, which provides an external intensified unidirectional magnetic field. With such intensified external field, preferably adjacent a planar scanning surface, successive partial areas of larger parts may be separately magnetized to reduce overall power consumption requirements and device size requirements. Thus, it is an object to provide apparatus and method which does not necessitate simultaneous magnetization of an entire workpiece to be tested.

Another object is improved apparatus which is readily portable or mobile, while having general purpose application to various magnetizable workpiece sizes and shapes. Further, a present object is to provide a device which may be used in either a handheld or fixed-mount configuration, as well as with either wet or dry magnetic particle inspection media, and further as well as with residual or continuous particle inspection methodologies. When used in a fixed-mount configuration, it is intended that the present invention may alternatively be used in conjunction with either of an automated or semiautomated testing system.

Still a further object is to provide a device which can operate on AC or rectified AC (i.e., half-wave DC) power. Also, it is an object to provide a device which is useful in subsequent demagnetization of tested magnetizable workpieces.

Various embodiments in accordance with the present invention may comprise different combinations of presently discussed and disclosed features, aspects, and steps in accordance with this invention. One such exemplary embodiment concerns a magnetizing head, comprising a coil, having a plurality of turns, for producing a magnetic field responsive to a flow of current therethrough; and a ferromagnetic core associated with such coil such that portions of the core reside between adjacent turns of the coil so as to intensify and direct the magnetic field outward from the head. With such an arrangement, a magnetic field is created external to the magnetizing head for adequately magnetizing at least a portion of a workpiece situated relatively adjacent the head for magnetic particle inspection of such workpiece.

Another exemplary embodiment in accordance with this invention is directed to a device for generating a magnetic field adapted for use in nondestructive magnetic particle inspection of a workpiece. The device comprises a controllable magnetizing head with a primary scanning surface to be moved relatively near a workpiece to be inspected. The head preferably includes coil means with plural windings respectively separated by ferromagnetic core members for controllably producing a unidirectional magnetic field external to the head adjacent the primary scanning surface thereof. Such magnetic field is preferably adequate for magnetizing at least part of the workpiece to be inspected with magnetic particles, without any contact between such workpiece and the magnetizing head.

Yet another apparatus for magnetic particle testing of a workpiece, in accordance with the present invention, comprises a generally rectangular scanner head, coil means associated with the scanner head, and conductor means for interconnecting the coil means with a power supply. Such scanner head preferably has at least one substantially planar surface comprising a scanning surface to be moved relative to a workpiece to be tested. The coil means associated with the scanner head preferably is responsive to current energization thereof for producing a generally unidirectional magnetic field external to the scanner head adjacent to the scanning surface thereof. The conductor means which interconnects the coil means with a power supply provides energizing current to such coil means. With the foregoing configuration, manipulation of a workpiece adjacent the scanning surface during production of the magnetic field permits multi-axis magnetization and subsequent demagnetization of a workpiece for magnetic particle testing of such workpiece, without any electrical or physical contact with such workpiece.

Still further aspects of the present invention more particularly concern a method or process of using a device in accordance with the present invention. One method of magnetic particle testing a magnetizable workpiece to detect discontinuities therein, in accordance with this invention, comprises the steps of providing a flux scanner head having an energizable coil of plural turns with ferromagnetic core members separating such turns, such coil when energized producing a unidirectional magnetic field external to the head; energizing the coil while associating a magnetizable workpiece with the unidirectional magnetic field produced therewith, without electrically or physically contacting the scanner head with such workpiece, so as to magnetize at least part of such workpiece along a selected first direction thereof; and performing magnetic particle testing on the magnetized workpiece to detect discontinuities residing in such workpiece at at least some significant angle to the first direction thereof.

Further present methodology includes the foregoing stated method, additionally combined with the step of repeating the energizing and associating step at least once, with the workpiece rotated at least about 45° from the first direction thereof, and successively repeating the magnetic particle testing step after each energizing and associating step repeat. With such a foregoing further method, multi-axis magnetic particle testing of a magnetizable workpiece, regardless of the complexity or size of its shape, may be performed in successive steps with a single flux scanner head without any electrical or physical contact between such scanner head and the workpiece being tested.

Those of ordinary skill and the art will appreciate that various modifications and variations to the foregoing specifically recited features and aspects and others of this invention may be practiced. Moreover, it is intended that all such modifications, including such as reversal of parts, or substitution of equivalent features or steps, come within the spirit and scope of the present invention, by virtue of present reference thereto.

BRIEF DESCRIPTION OF THE DRAWINGS

A complete and enabling disclosure of the present invention, including the best mode thereof, to those of ordinary skill in the art is set forth in the following specification with reference to the accompanying drawings, in which.

Repeat use of reference characters in the following specification and accompanying drawings is intended to represent same or analogous features or elements of the invention.

DETAILED DESCRIPTION OF THE PREFERRED EMBODIMENTS

Those of ordinary skill in the art will appreciate that the following discussion is intended by way of example only with reference to the presently disclosed exemplary embodiments, and is not intended to limit the broader teachings of the invention set forth herein. More particularly, it is to be understood that the practice of additional features or steps beyond those set forth or suggested herein is not precluded by any present omission thereof. It is also not considered necessary to discuss every detail of the broad concepts of magnetic particle inspection techniques, since such general techniques as referred to herein are considered well known to those skilled in the art of such nondestructive testing.

Figure 1:
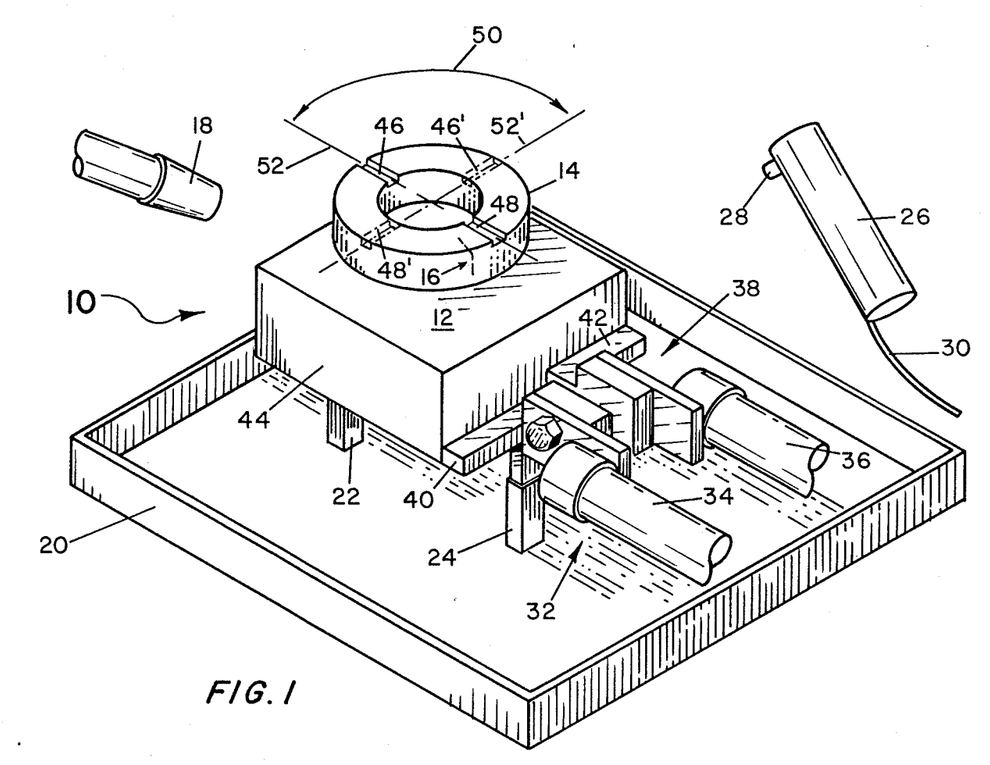
FIG. 1 is a perspective view of a magnetizing head in accordance with the present invention, and arranged for a method of use in accordance with the present invention, in a generally fixed-mount configuration for wet magnetic particle application to an exemplary annular workpiece to be tested.

FIG. 1 illustrates a perspective view of the present invention, including use of same with methodology in accordance with this invention. More specifically, a magnetizing head or device 10 for generating a magnetic field is represented in its preferred generally rectangular form. The construction of flux scanner head 10, which is not strictly limited to a rectangular form, is discussed below in greater detail with reference to present FIGS. 3 through 5. In general, an embedded coil having a plurality of windings is associated with a magnetic core having members or portions that reside between the adjacent turns of the coil so as to intensify and direct a magnetic field outward from the scanner head, as represented below in conjunction with present FIG. 3.

In effect, the coil arrangement comprises coil means for producing a generally unidirectional magnetic field external to the scanner head adjacent to a preferably planar scanning surface 12 thereof. Numerous advantages flow from the generation of an intensified external unidirectional magnetic field, as alluded to above in the Summary of the Invention portion of this application. For example, adequate magnetization of a magnetizable or ferromagnetic workpiece 14 may be obtained without electrical or physical contact between workpiece 14 and scanner head 10. Once such adequate magnetization is produced, discontinuities within or on the surface of workpiece 14, as exemplified by peripheral crack 16 in present FIG. 1, may be detected with magnetic particle inspection.

To complete representation of the present methodology, and exemplary spray nozzle 18 is illustrated for use in conjunction with applying magnetic particles to the workpiece to be tested. While the present invention may be practiced with either residual or continuous methods, as well as with wet or dry magnetic particle applications, the known wet fluorescent continuous magnetic particle inspection method is presently preferred. For use with such wet methods, a basin 20 or the like is represented for collection of the flow of materials from nozzle 18, as understood by those of ordinary skill in the art.

As represented in present FIG. 1, the scanner head 10 is utilized in a relatively fixed-mount configuration, supported on members 22 and 24, which are preferably adapted for alternatively serving in manipulation and support of scanner head 10 when same is used in a handheld configuration. In such handheld use, member 26 may be received in conjunction with (in any convenient manner) members 22 and 24 to serve as handle means for scanner head 10. While any convenient electrical control may be used in conjunction with a conventional power supply for supplying power to scanner head 10, an electrical switch or the like 28 received on removable handle element 26 may be used to switch power to scanner head 10 via a control line 30. Conductor means 31, preferably including a pair of power cables 34 and 36, literally interconnects the coil means embedded in scanner head 10 with a power supply (not shown) to provide energizing current to produce the magnetic field referred to above for magnetizing workpiece 14. As is known to those of ordinary skill in the art, relatively high levels of current are involved with production of magnetic fields adequate to magnetize the ferromagnetic workpieces to be tested. Accordingly, relatively heavy gauge power cables, as well as connecting elements (generally 38) are preferred. The specific interconnection of the conductor members 40 and 42 of conductor means 32 with coil means in accordance with this invention is discussed in greater detail below with reference to present FIG. 4.

The exemplary scanner head 10 represented in FIG. 1 may assume various sizes. Generally, one exemplary embodiment capable of producing an adequate magnetic field for use in conjunction with magnetic particle inspections is about 5 inches in length along its longitudinal length (for scanner head 10), is about 3½ inches wide and about 2 inches thick. Exemplary dimensions of windings, core members, and other aspects of the scanner head 10 interior construction are discussed below with reference to FIGS. 3 through 5. For the general protection of scanner head 10, a relatively thin protective coating or layer, such as a polymerized encasement 44, may be sealed about the entire outer surface of scanner head 10.

As further represented in present FIG. 1, an annular workpiece 14 may be thoroughly tested in several successive steps by successively energizing scanner head 10 to produce a magnetic field acting on workpiece 14 in several successive positions thereof. The need for relative movement between a given workpiece and magnetizing device is well known to those of ordinary skill in the art, based on the fact that a discontinuity or crack generally in alignment with the direction of the magnetic field will not be detected through magnetic particle inspection. In other words, some significant angle, such as 45° or more must be in existence between the cracks to be detected and the direction of the magnetic field applied thereto. With the intensified external magnetic field generated by the present scanner head, even a relatively complex shaped piece such as annular piece 14 with slots 46 and 48 may be quickly and conveniently tested. Double headed arrow 50 represents rotation, such as by 90°, of workpiece 14 between successive energization and testing step repeats. For example, the axis of channels 46 and 48 may initially be aligned along line 52, and then rotated to the positions 46' and 48' in alignment with line 52'.

Virtually without limitation, other workpieces of various sizes and shapes, may be magnetized for testing, with practice of the present invention. Those of ordinary skill in the art are well acquainted with positioning techniques of workpieces relative the magnetic field being generated, without detailed discussion thereof herein. As one example, small diameter shafts, such as having less than ½ inch diameter, may be rested on a stand relative flux scanner head 10, which would in part serve as flux concentrator rails.

In the case of the exemplary scanner head dimensions discussed above, an article such as the workpiece 14 illustrated in FIG. 1, may be adequately magnetized by positioning same (fixed or moving) within about 1 inch over scanning surface 12, while energizing coil means within scanner head 10 with about 750 amperes of AC power. A conventional power supply normally automatically regulates the voltage level, which is typically kept relatively low, such as around 20 volts. Indications of discontinuities can be obtained in a much broader range of amperage levels, such as from about 100 to as much as 10,000 amperes (or sometimes even higher). As is known, generally the larger or thicker the workpiece, the higher level of current which is required.

One advantage of the present invention is that workpieces much larger than the scanner head itself may be successively magnetized in selected partial regions thereof, until the entire work piece is adequately covered. Without the need of simultaneously magnetizing the entire workpiece, power consumption requirements can in some instances be greatly reduced. As a result, portability of the present invention is gained, and the size of the associated requisite power supply may in turn be reduced. A conventional power supply, using either AC or half-wave DC, may be used in combination with the present invention. One example of such a power supply is represented by energy source 50 disclosed in U.S. Pat. No. 4,694,247, issued to Meili et al. as generally discussed above, the disclosure of which is incorporated herein by reference.

Figure 2:
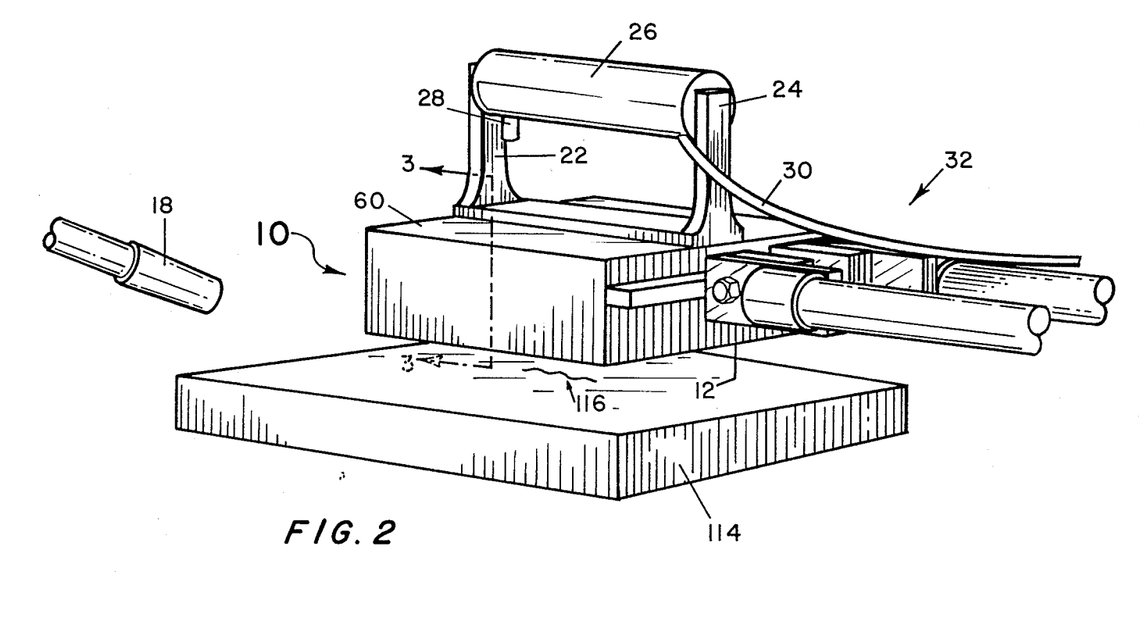
FIG. 2 is another perspective view of the present device as illustrated in FIG. 1, in accordance with present methodology, configured for use in a hand-held arrangement for testing an exemplary generally planar workpiece.

In addition to the foregoing portability advantage, the present invention may be used in fixed-mount or permanently installed configurations, with or without an automated or semi-automated testing system. The present invention may also be practiced in a hand-held configuration. Present FIG. 2 represents use of the present exemplary flux scanner 10 in such an exemplary hand-held configuration. In the perspective illustration of present FIG. 2, scanning surface 12 is not seen directly since it is underneath scanner head 10, which is turned "down" towards generally planar workpiece 114, which has an illustrated exemplary crack 116 showing in a surface thereof. In this configuration, support members 22 and 24 are adapted for receiving handle member 26, and are in turn mounted on a second generally planar surface 60 of scanner head 10 which is generally opposite to the first generally planar surface 12 thereof. Alternative associations of members 22 and 24 with scanner head 10 may be practiced, so long as means for manipulating scanner head 10 in a hand-held configuration are provided.

As represented by present FIG. 2, workpiece 114 is at least as large, if not larger, than scanner head 10 itself. Thus, relative movement between the scanner head and the workpiece may be desired to effect complete coverage of such workpiece, without requiring electrical or physical contact between the two. Of course, successive magnetization steps may be practiced with the orientation between the workpiece and the magnetic field generated by magnetizing head 10 rotated at least about 45° (and preferably about 90°) to insure detection of any cracks or discontinuities in workpiece 114. As discussed below with reference to FIG. 3, generally the unidirectional magnetic field emanating from scanning surface 12 is perpendicular to the exemplary crack 116 as illustrated in FIG. 2. Thus, such crack would be detected during magnetic particle inspection, such as including application of fluidly suspended magnetic particles from nozzle 18.

With electrical switch 28 mounted directly on handle 26, generation of such magnetic field is conveniently controlled while scanner head 10 is manipulated in such hand-held configuration. Again, considerable advantage is gained with the intensified external unidirectional magnetic field generated by scanner head 10, in that workpieces of various sizes and shapes may be quickly and thoroughly processed, even without physical or electrical contact between the workpiece and the scanner head.

Figure 3:
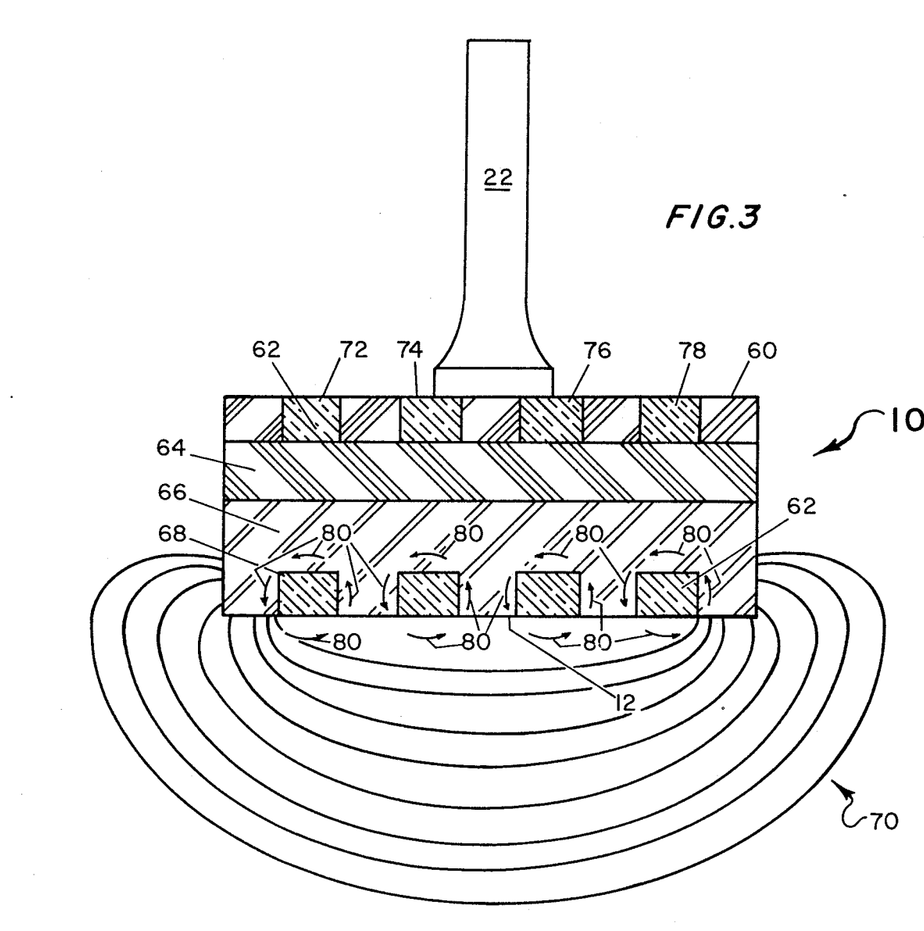
FIG. 3 is a cross-sectional view of the exemplary magnetizing head or device in accordance with the present invention per FIG. 2, taken along the line 3—3 as shown in such FIG. 2.

Present FIG. 3 represents a lateral cross-section of the exemplary scanner head in FIG. 2, taken along the line 3—3 illustrated therein. Such Figure also illustrates the support member 22 in relation to scanner head 10, and represents magnetic lines of force generated by energization of the coil means of scanner head 10.

In FIG. 3, a number of different sectional lines are utilized to represent the different components of the exemplary scanner head. For example, the areas designated by markings 62 represent materials forming coils means in accordance with this invention, while the material designated by reference character 64 illustrates insulated material, and the material designated by reference character 66 represents ferromagnetic core means in accordance with this invention. Insulated barriers preferably reside between the coil material 62 and core material 66, as designated by reference character 68. Like sectional lines in different areas represent similar or analogous materials in such different areas.

It is known to those of ordinary skill in the art that copper is a preferred central conductor for use in magnetic particle inspection techniques, because there is less heat build up at the high current levels involved, due to better conductivity of copper. Accordingly, it is preferred that copper bar stock or the like be used in the coil material 62 represented herewith, though windings or turns of aluminum wire or the like may be alternatively practiced. The insulated barriers and insulator material represented in present FIG. 3 may comprise virtually any material having insulative value. One example would be wood or pulp material, such as black walnut wood.

One preferred ferromagnetic core material is iron. In accordance with this invention, the core means includes members or portions thereof residing between adjacent turns of the coil means on at least one side of the coil. The FIG. 3 representation is intended as representing an iron core makeup of thin, ferromagnetic plates shaped to fit behind and between the windings or turns of the coil on one side of the coil. With material 68, such plates are electrically insulated from the turns of the coil and from each other. Thus, the magnetic field 70 produced by current flow through the coil is intensified and directed outward and externally from the scanning surface 12 of scanner head 10. Alternatively, core material 66 may comprise a solid core of ferromagnetic material occupying an area as represented in FIG. 3.

While various numbers of windings or turns may be practiced in accordance with this invention, the number of such turns are preferably in a range of from about 3 to about 5 turns. FIG. 3 represents an exemplary construction utilizing 4 turns, generally 72, 74, 76, and 78. In the preferred illustrated embodiment wherein copper bar stock is used for establishing the perspective windings of the coil means, elements of copper bar stock embedded near surfaces 12 and 60 of scanner head 10 are mutually aligned for a given turn of the coil means. However, the interspaced core material between the windings is so associated on only one side of the coil (i.e., adjacent scanning surface 12 thereof), while insulative material is instead interspaced between coil turns adjacent planar surface 60.

Current flowing through each of the turns generates a magnetic field circular in character about such conductor, and relatively strongest near the surface of such conductor, as represented by the plural lines of magnetic force 80 illustrated about each of the copper bar stock portions of turns 72, 74, 76, and 78 adjacent surface 12 of scanner head 10. With the illustrated interrelationship between coil turns and core members as illustrated in present FIG. 3, the unidirectional field 70 is generated in an intensified condition external to surface 12, for magnetization of workpieces for magnetic particle inspection thereof, as discussed above with reference to FIGS. 1 and 2. In other words, once magnetized, the flux leakage occurring at cracks or other discontinuities in the workpiece will cause magnetic particles to be attracted to such leakages, thereby permitting visual detection of same.

Depending on the type and level of current passed through the coil means, magnetic field 70 may obtain the character of and be used as a demagnetizing field in connection with the tested workpiece. In general, this is accomplished by using AC current and relatively moving the workpiece through the demagnetizing field while relatively slowly reducing the current level. Use of the AC current reverses the existing or residual fields retained in a workpiece, which tends to eliminate such residual fields, as does the ever reducing level of the magnetic field produced during lowering of the energizing current.

Figure 4:
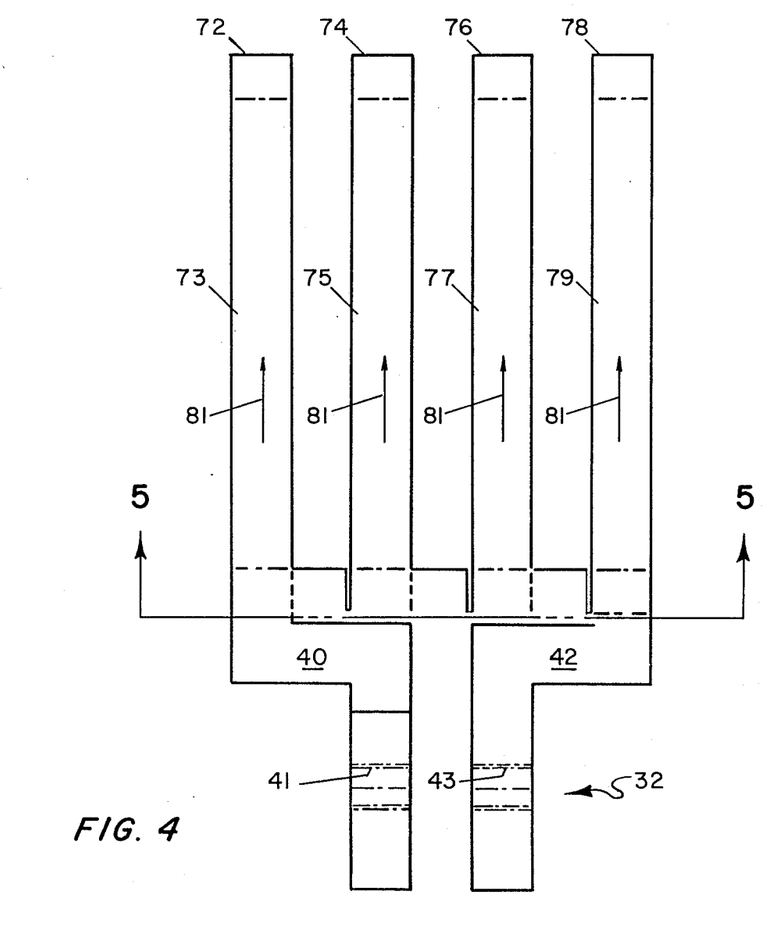
FIG. 4 is a top plan view of an exemplary coil arrangement in accordance with present invention, as would be embedded within the exemplary magnetizing head of FIGS. 1 through 3.
Figure 5:
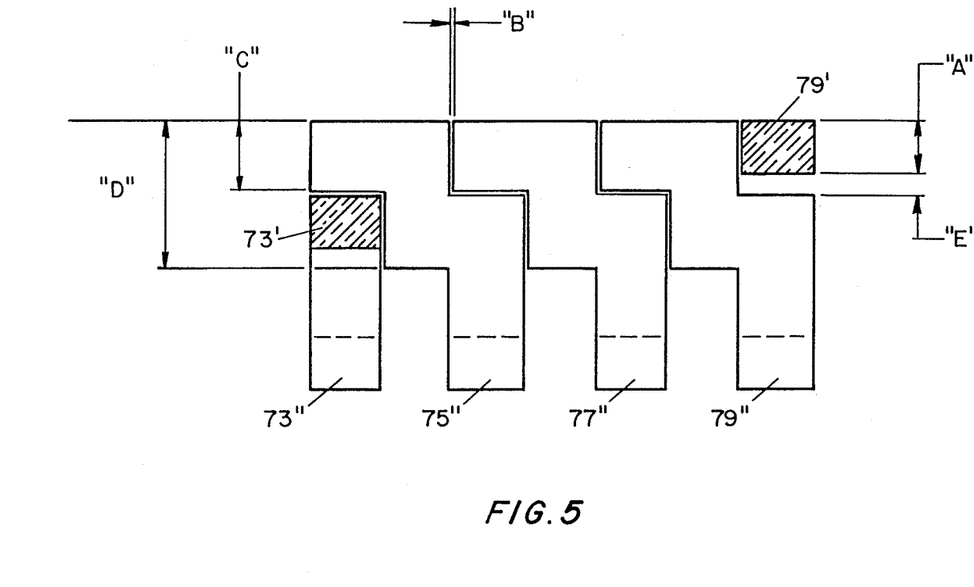
FIG. 5 is a cross-sectional view of the present exemplary coil means of FIG. 4, taken along the line 5—5 as indicated in such Figure.

While none of the figures herewith are intended as being drawn to strict scale, the general relationships and relative dimensions discussed in the body of this specification are reflected by the relative features of the illustrations. While present FIG. 3 represents a cross-sectional illustration of the scanner head components, such cross-sectional configuration is generally continuous along the length of the scanner head. FIG. 4 is intended as a top plan view of the coil means features only as represented in present FIG. 3, for clarity in illustration thereof. FIG. 5 is similarly a view of such coil means features only, taken along the line 5—5 as illustrated in such FIG. 4.

The copper bar stock represented in FIGS. 4 and 5 may preferably have a width of about ½ inch and a thickness of about ⅜ inch nominally. See width A in FIG. 5.

The invention is not limited to a specific number of turns or windings, but the exemplary embodiment illustrated herein includes four (4) such windings 72, 74, 76, and 78. All of the windings are interconnected to conductor means 32 through elements 40 and 42 thereof. Such elements may comprise any type of conductor materials, and may be connected through virtually any type of connectors to incoming power cables. One heavy duty connector includes a mount with threaded openings 41 and 43 to receive securement elements such as screws or the like. Such features may be varied to accommodate specific design needs or other user requirements.

The dotted line representations in FIGS. 4 and 5 relative the exemplary copper bar stock members are intended to represent the placement elements beneath those elements seen in the top plan view of FIG. 4. For example, the members 73, 75, 77, and 79 illustrated would correspond with the runs of the windings adjacent surface 60 of a given scanner head. Current flow arrows 81 are represented in each of such members, resulting in exemplary magnetic field 70 discussed above in conjunction with present FIG. 3. As is further represented in FIG. 4, connector members 40 and 42 directly interconnect with respective end portions of copper bar stock members 73 and 79, with such connection being represented by cross sectional surfaces 73' and 79' in present FIG. 5.

Turning attention now more completely to such FIG. 5, further copper bar stock members perpendicular to the length-wise copper bar stock members adjacent surfaces 12 and 60 are illustrated as interconnecting such respective runs defining each turn of the coil means. In FIG. 4, the copper bar stock members adjacent surface 12 are not seen because they lie respectively directly beneath their corresponding members adjacent planar surface 60. However, in FIG. 5, such members are designated respectively 73", 75", 77", 79". Gaps as represented by width B permit the interspersing of insulative barriers within the magnetizing head, as discussed above. A typical gap would be 0.015 inches, though variation may be practiced. A width of designated region C in FIG. 5 may be nominally ½ inches, while the width of adjacent region D may be about 1.03 inches. On the opposite side of FIG. E, the width of region E may be about 0.16 inches. All of the exemplary dimensions, materials, and operational power levels will enable one of ordinary skill in the art to both make and use a magnetizing head in accordance with this invention, further in accordance with the methodology also disclosed above.

While such specific exemplary details have been disclosed and discussed, modifications, and variations thereto within the broader teachings of this invention may be practiced. For example, a number of different operations may be undertaken to accomplish relative motion or successive movements of a workpiece relative a magnetizing head. Different types of conventional power supplies, utilizing both AC and various rectified AC-type power may be used, with different types of standard connectors or conductors between such power supply and the magnetizing head itself. Likewise, different degrees of rotation, such as at least 45° or higher may be practiced for successive energization and testing operations on a given workpiece. In none of such variations is it necessary to physically or electrically interconnect the workpiece to be tested with the magnetizing scanner head in accordance with the present invention. Accordingly, while exemplary details and possible variations have been disclosed and suggested, none of the foregoing is intended as limiting the present invention which is further set forth below in conjunction with the appended claims.

What is claimed is:

1. A magnetizing head, comprising:
    a coil, having a plurality of turns, for producing a magnetic field responsive to a flow of current therethrough; and
    a ferromagnetic core associated with said coil such that portions of said core reside between adjacent turns of said coil so as to intensify and direct said magnetic field outward from said head;
    wherein said coil and core form a generally rectangular body, with said coil turns generally defining at least part of the periphery of said rectangular body on at least two opposing surfaces thereof.

2. A magnetizing head as in claim 1, wherein said coil turns comprise copper bar stock with bar stock members of a given turn being mutually aligned.

3. A magnetizing head as in claim 1, wherein said core comprises a plurality of thin, ferromagnetic plates shaped to fit behind and between said coil turns on one side of said coil, with said plates being electrically insulated from said coil turns and from each other.

4. A magnetizing head as in claim 1 wherein said core comprises solid ferromagnetic material, having extending portions thereof projecting between adjacent turns of said coil on one side thereof.

5. A magnetizing head as in claim 1, further comprising an insulating plane received within said rectangular body intermediate to and parallel with said two opposing surfaces thereof, with said coil turns being received generally thereabout.

6. A magnetizing head as in claim 1, further comprising:
    conductor means interconnected with said coil for controllably providing a flow of AC or rectified AC power therethrough; and
    means associated with said magnetizing head for alternatively permitting manual handling of said head to selectively position same relative a workpiece, or for supporting said head to permit manipulation of a workpiece relative such supported magnetizing head.

7. A magnetizing head as in claim 1, wherein said coil turns comprise wrapped aluminum wires, and said ferromagnetic core comprises an iron core.

8. A magnetizing head as in claim 1, wherein said coil turns number generally from about 3 to about 5 turns, current flowing therethrough for producing said magnetic field is generally in a range of about 100 to about 10,000 amperes AC or half-wave AC.

9. A device for generating a magnetic field for use in nondestructive magnetic particle inspection of a workpiece, said device comprising a controllable magnetizing head with a primary scanning surface to be moved relatively near a workpiece to be inspected, said head including coil means with plural windings respectively separated by ferromagnetic core members for controllably producing a unidirectional magnetic field external to said head adjacent said primary scanning surface thereof, which magnetic field is adequate for magnetizing at least part of the workpiece to be inspected with magnetic particles, without any contact between such workpiece and said magnetizing head, wherein said plural windings comprise members in mutual alignment in a given turn and situated within said magnetizing head adjacent peripheral surfaces thereof.

10. A device as in claim 9, wherein:
said plural windings, comprise respective turns of copper bar stock comprising said members, with such bar stock in a given turn being in mutual alignment and situated within said magnetizing head adjacent peripheral surfaces thereof; and
said ferromagnetic core members comprise respective thin plates shaped to fit behind and between said copper turns on one side of said coil.

11. A device for generating a magnetic field, comprising:
a controllable magnetizing head with a primary scanning surface to be moved relatively near a workpiece to be inspected, said head including coil means with plural windings respectively separated by ferromagnetic core members for controllably producing a unidirectional magnetic field external to said head adjacent said primary scanning surface thereof, which magnetic field is adequate for magnetizing at least part of the workpiece to be inspected with magnetic particles, without any contact between such workpiece and said magnetizing head; and
a pair of power cables interconnected with said coil means to provide power thereto for producing said unidirectional magnetic field; and
handle means associated with said magnetizing head for alternately permitting manipulation thereof, and support thereof, for movement relative thereto of the workpiece to be inspected, which handle means further includes a controllable switch to permit control of said coil means operation, wherein said handle means renders said device portable, with power supplied thereto from a transportable power supply through said power cables.

12. A device as in claim 9, further including an encasement such as polymerized materials surrounding said head for the protection thereof.

13. Apparatus for magnetization of a workpiece for subsequent magnetic particle testing thereof, comprising:
a generally rectangular scanner head, having at least one substantially planar surface comprising a scanning surface to be moved relative to a workpiece to be tested;
coil means, associated generally with said scanner head scanning surface and responsive to current energization thereof, for producing a generally unidirectional magnetic field external to said scanner head adjacent to said scanning surface thereof; and
conductor means for interconnecting said coil means with a power supply to provide energizing current thereto, wherein manipulation of a workpiece adjacent said scanning surface during production of said magnetic field permits multi-axis magnetization and subsequent demagnetization of a workpiece for magnetic particle testing of such workpiece, without any electrical or physical contact with such workpiece.

14. An apparatus as in claim 13, wherein:
said scanner head includes a second substantially planar surface on a side thereof opposite said one planar surface thereof, and said coil means include a plurality of copper bar stock members embedded respectively in said first and second planar surfaces, with respective copper bar stock members being aligned and interconnected by further copper bar stock members perpendicular thereto for forming a plurality of interconnected turns comprising said coil means; and
wherein said apparatus further includes ferromagnetic core means within said scanner head, with plural elements of said core means interspaced between said copper bar stock members embedded in said one planar surface of said scanner head.

15. An apparatus as in claim 14, further including a plurality of insulative barrier members provided between said copper bar stock members embedded in said second planar surface of said scanner head, and further including an insulator layer received within said scanner head intermediate and parallel to said first and second planar surfaces thereof.

16. An apparatus as in claim 14, wherein said core means comprises a plurality of thin, ferromagnetic plates, shaped to fit behind and between said copper bar stock members on the side of said coil adjacent to said scanner head one planar surface.

17. An apparatus as in claim 14, wherein said number of coil means turns is from about 3 to about 5, and said generally rectangular scanner head has dimensions of approximately 5 inches by 3½ inches by 2 inches.

18. An apparatus as in claim 13, wherein said conductor means comprise a pair of power cables of adequate gauge for carrying AC or half-wave rectified DC in a range of generally from about 100 to about 10,000 amperes.

19. An apparatus as in claim 13, further including support members associated with said scanner head for alternatively configuring same for hand-held or fixed-mount use, and a handle member removably mounted on said support members and incorporating thereinto a switch for controlling current energization of said coil means though said conductor means.

20. A method of magnetizing a magnetizable workpiece to detect discontinuities therein with magnetic particle testing, such method comprising the steps of:
providing a flux scanner head with a scanning surface having an energizable coil of plural turns thereat with ferromagnetic core means for separating such turns, said coil when energized producing a unidirectional magnetic field external to said head scanning surface;
energizing said coil and associating a magnetizable workpiece with the unidirectional magnetic field produced therewith, without electrically or physically contacting said scanner head with such workpiece, so as to magnetize at least part of such workpiece along a selected first direction thereof.

21. A method as in claim 20, further including:
performing magnetic particle testing on the magnetized workpiece to detect discontinuities residing in such workpiece at least some significant angle to said first direction thereof; and
repeating said energizing and associating step at least once, with the workpiece rotated at least about 45° from said first direction thereof, and successively repeating said magnetic particle testing step after each energizing and associating step repeat, whereby multi-axis magnetic particle testing of a magnetizable workpiece, regardless of the complexity or size of its shape, may be performed in successive steps with a single flux scanner head without any electrical or physical contact between such scanner head and the workpiece being tested.

22. A method as in claim 21, wherein such workpiece rotation includes rotating said workpiece approximately 90° from said first direction thereof prior to repeat of said energizing and associating step.

23. A method as in claim 21, wherein said magnetic particle testing step includes a continuous magnetic particle testing method.

24. A method as in claim 23, wherein said continuous magnetic particle testing method includes a wet fluorescent continuous method.

25. A method as in claim 21, wherein said magnetic particle testing step includes a residual magnetic particle testing method.

26. A method as in claim 20, wherein energizing said coil includes supplying one of AC or half-wave rectified DC to said coil in a range from generally about 100 to about 10,000 amperes.

27. A method as in claim 26, wherein:
said energizing includes supplying said coil with about 750 amperes of AC power, and said associating includes one of movement or placement of a magnetizable workpiece over said flux scanner head scanning surface approximately one inch away from said scanning surface.

28. A method as in claim 21, further including a plurality of energizing, associating, and testing step repeat sequences successively undertaken in respective, plural partial locations of a magnetizable workpiece in sum adequate to subject the entirety of such workpiece to magnetic particle testing, whereby relatively lower power consumption is required for testing relatively larger workpieces.

29. A method as in claim 20, wherein said associating includes holding a workpiece relatively fixed in relation to said magnetic field during energizing of said coil.

30. A method as in claim 20, wherein said associating includes relatively moving a workpiece in relation to said magnetic field during energizing of said coil.

31. A method as in claim 20, wherein said associating includes moving said flux scanner head over a magnetizable workpiece while such workpiece is relatively fixedly supported.

32. A method as in claim 20, wherein said associating includes relatively fixedly supporting said flux scanner head and moving a magnetizable workpiece over such relatively fixedly supported flux scanner head.

33. A method as in claim 21, further including the step of demagnetizing the magnetizable workpiece upon completion of such testing, including establishing a demagnetizing field by energizing said coil with a decreasing amount of AC power while associating the magnetized, tested workpiece with such demagnetizing field thereby produced with said coil.

34. A method as in claim 20, wherein said flux scanner head providing step includes providing a coil having from about 3 to about 5 turns comprising copper bar stock, with bar stock members of a given turn mutually aligned within said scanner head, and further including providing a plurality of thin, ferromagnetic plates shaped to fit behind and between said coil turns on one side of said coil, with said plates being electrically insulated from said coil turns and from each other.

* * * * *